US011066530B2

(12) United States Patent
DiBella, Jr. et al.

(10) Patent No.: US 11,066,530 B2
(45) Date of Patent: Jul. 20, 2021

(54) OPHTHALMIC DEVICES CONTAINING UV BLOCKER AND METHODS FOR THEIR PREPARATION

(71) Applicant: Bausch & Lomb Incorporated, Rochester, NY (US)

(72) Inventors: James Anthony DiBella, Jr., Macedon, NY (US); George L. Grobe, III, Ontario, NY (US); Alok Kumar Awasthi, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 248 days.

(21) Appl. No.: 16/361,947

(22) Filed: Mar. 22, 2019

(65) Prior Publication Data

US 2019/0339544 A1    Nov. 7, 2019

Related U.S. Application Data

(60) Provisional application No. 62/665,148, filed on May 1, 2018.

(51) Int. Cl.
| | |
|---|---|
| *G02C 7/04* | (2006.01) |
| *B29D 11/00* | (2006.01) |
| *C08J 7/06* | (2006.01) |
| *G02B 1/04* | (2006.01) |
| *A61L 12/08* | (2006.01) |
| *A61L 12/12* | (2006.01) |
| *B29L 11/00* | (2006.01) |
| *C08F 290/06* | (2006.01) |

(52) U.S. Cl.
CPC .......... *C08J 7/065* (2013.01); *B29D 11/00038* (2013.01); *G02B 1/043* (2013.01); *G02C 7/04* (2013.01); *A61L 12/086* (2013.01); *A61L 12/124* (2013.01); *B29L 2011/0041* (2013.01); *C08F 290/068* (2013.01)

(58) Field of Classification Search
CPC ............... A61L 12/086; A61L 12/124; B29D 11/00038; B29D 11/023; B29D 11/00894; B29L 2011/0041; C08F 290/068; C08J 2383/04; C08J 7/065; C08K 5/3475; G02C 7/04; G02C 7/10; G02B 1/043
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 4,113,224 A | 9/1978 | Clark et al. |
| 4,136,250 A | 1/1979 | Muelier et al. |
| 4,153,641 A | 5/1979 | Deichert et al. |
| 4,197,266 A | 4/1980 | Clark et al. |
| 4,559,059 A | 12/1985 | Su |
| 4,740,533 A | 4/1988 | Su et al. |
| 4,910,277 A | 3/1990 | Bambury et al. |
| 4,954,587 A | 9/1990 | Mueller |
| 5,010,141 A | 4/1991 | Mueller |
| 5,034,461 A | 7/1991 | Lai et al. |
| 5,070,215 A | 12/1991 | Bambury et al. |
| 5,079,319 A | 1/1992 | Mueller |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,358,995 A | 10/1994 | Lai et al. |
| 5,387,662 A | 2/1995 | Kunzler et al. |
| 5,449,729 A | 9/1995 | Lai |
| 5,512,205 A | 4/1996 | Lai |
| 5,681,871 A | 10/1997 | Molock et al. |
| 6,162,844 A | 12/2000 | Lally et al. |
| 9,249,249 B2 | 2/2016 | Awasthi et al. |
| 2005/0283234 A1 | 12/2005 | Zhou et al. |
| 2009/0142485 A1 | 6/2009 | Lai et al. |
| 2010/0178316 A1 | 7/2010 | Chauhan et al. |
| 2014/0178595 A1* | 6/2014 | Bothe .............. B29D 11/00865 427/512 |
| 2014/0288206 A1 | 9/2014 | Chauhan et al. |
| 2018/0341043 A1 | 11/2018 | Kawaguchi et al. |

FOREIGN PATENT DOCUMENTS

| | | |
|---|---|---|
| EP | 1134071 A2 | 9/2001 |
| EP | 1323743 A2 | 7/2003 |
| JP | 2005292240 A | 10/2005 |
| WO | 96/31792 A1 | 10/1996 |
| WO | 2017047742 A1 | 3/2017 |
| WO | 2017048726 A1 | 3/2017 |
| WO | PCT/US19/23627 | 6/2019 |

OTHER PUBLICATIONS

Lai, Yu Chin, "The Role of Bulky Polysiloxanylalkyl Methacrylates in Polyurethane-Polysiloxane Hydrogels," Journal of Applied Polymer Science, vol. 60, 1193-1199 (1996).

* cited by examiner

*Primary Examiner* — Tuyen Tra
(74) *Attorney, Agent, or Firm* — Ryan, Mason & Lewis, LLP

(57) ABSTRACT

A method for preparing an ophthalmic device containing an ultraviolet (UV) blocker is disclosed. The method involves (a) soaking an ophthalmic device in one or more first solvent solutions to swell the ophthalmic device; (b) soaking the swelled ophthalmic device in one or more second solvents solutions comprising a UV blocker to de-swell the ophthalmic device and entrap the UV blocker in the ophthalmic device, wherein the UV blocker is a benzotriazole and (c) sterilizing the de-swelled ophthalmic device.

38 Claims, No Drawings

OPHTHALMIC DEVICES CONTAINING UV BLOCKER AND METHODS FOR THEIR PREPARATION

BACKGROUND

The present invention generally relates to ophthalmic devices containing an ultraviolet light (UV) blocker and methods for their preparation.

It is well known that sunlight may damage the human eye, especially in connection with the formation of cataracts and age-related macular degeneration which can lead to loss of vision. To minimize UV damage to the eyes, a subject can wear eye glasses or contact lenses that are protective against peripheral radiation. The degree of blocking however depends on the type of lens and the design of the sunglasses. Most styles of sunglasses do not offer complete protection from UV radiation, thereby allowing UV light to reach the eyes around the frames of the eyeglasses. By wearing UV blocking contact lenses, which cover the entire cornea, UV protection from all angles can be obtained.

In the fraction of sunlight, the long wave and near ultraviolet (UVA and UVB) range are most concerned, which are characterized by wavelength of 280 to 380 nanometers (nm). The U.S. Food and Drug administration (FDA) has established standards for UV blocking contact lenses based on American National Standards Institute (ANSI) standards. In particular, the FDA classifies UV blocking contact lenses into two categories, Class I and Class II, depending on the extent of the protection. Class I contact lenses must block more than 90% of UVA i.e., 316 to 380 nm for UVA, and 99% of UVB, i.e., 280 to 315 nm, radiation. Class II lenses must block more than 50% of UVA and 95% of UVB radiation. Although UVA radiation corresponds to the wavelength range of 316-400 nm, only wavelengths from 316-380 nm are considered for classification of a contact lens.

The major challenges in preparing a contact lens loaded with a UV absorber include, for example, preparing the lens with short curing times at reasonable light intensities to avoid any undesired side reactions, maintaining the clarity and uniformity of the lens and the UV absorber over the entire area of the lens, and avoiding any leaching of the UV absorber from the lens.

Accordingly, as there are currently only a few commercially available contact lenses that are approved as Class I UV blockers, there remains a need to develop effective Class I UV blocking contact lenses.

SUMMARY

In accordance with one embodiment of the present invention, there is provided a method for preparing an ophthalmic device containing an ultraviolet (UV) blocker comprising:

(a) soaking an ophthalmic device in one or more first solvent solutions to swell the ophthalmic device;

(b) soaking the swelled ophthalmic device in one or more second solvents solutions comprising a UV blocker to de-swell the ophthalmic device and entrap the UV blocker in the ophthalmic device, wherein the UV blocker is a benzotriazole of the general formula I:

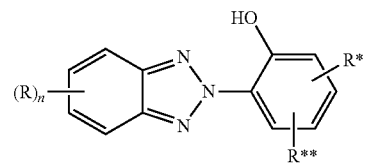

wherein each R is independently hydrogen, a halogen, an —O— group, a nitro group, a nitrile group, an alkoxy group, a hydroxyl group, an alkyl group, a cycloalkyl group, an alkenyl group, an alkynyl group, an aromatic group, an amine group, a carbonyl group, and a heterocyclic group, R* is a linear or branched $C_3$ to $C_{28}$ alkyl, a nitro group, a nitrile group, an alkoxy group, a hydroxyl group, a cycloalkyl group, an alkenyl group, an alkynyl group, an aromatic group, an amine group, a carbonyl group, and a heterocyclic group, and R** is a linear $C_1$ to $C_8$ alkyl group, a branched $C_3$ to $C_8$ alkyl, a halogen, a nitro group, a nitrile group, an alkoxy group, a hydroxyl group, a cycloalkyl group, an alkynyl group, an alkenyl group, an aromatic group, an amine group, a carbonyl group, and a heterocyclic group; and (c) sterilizing the de-swelled ophthalmic device.

In accordance with a second embodiment of the present invention, there is provided a method for preparing an ophthalmic device containing an UV blocker comprising:

(a) soaking an ophthalmic device in one or more first solvent solutions to swell the ophthalmic device;

(b) soaking the swelled ophthalmic device in one or more second solvent solutions comprising a UV blocker of general formula I to de-swell the ophthalmic device and entrap the UV blocker in the ophthalmic device;

(c) soaking the de-swelled ophthalmic device in water to further de-swell the ophthalmic device; and (d) sterilizing the de-swelled ophthalmic device.

In accordance with a third embodiment of the present invention, there is provided an ophthalmic device comprising a UV blocker of general formula I entrapped in a polymerization product of a monomeric mixture comprising one or more ophthalmic device-forming monomers.

The present invention is based on the surprising discovery that by employing the method described herein a UV blocker will be entrapped into an ophthalmic device, such as a contact lens, and not leach out. The present invention is also based on the surprising discovery that the resulting UV blocking ophthalmic device demonstrates sufficient blocking of UV light to meet both FDA Class I and II specifications for UV blocking.

DETAILED DESCRIPTION

The present invention is directed to a UV blocking ophthalmic device demonstrating sufficient blocking of UV light to meet both FDA Class I and II specifications for UV blocking. As stated above, Class I contact lenses must block more than 90% of UVA i.e., 316 to 380 nm, radiation and 99% of UVB, i.e., 280 to 315 nm, radiation. Class II contact lenses must block more than 50% of UVA and 95% of UVB radiation. As used herein, the terms "ophthalmic device" and "lens" refer to devices that reside in or on the eye. These devices can provide optical correction, wound care, drug delivery, diagnostic functionality or cosmetic enhancement or effect or a combination of these properties. Useful ophthalmic devices include, but are not limited to, ophthalmic lenses such as soft contact lenses, e.g., a soft, hydrogel lens; soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking. The ophthalmic devices such as contact lenses of the present invention can be spherical, toric, bifocal, may contain cosmetic tints, opaque cosmetic patterns, combinations thereof and the like.

The ophthalmic devices according to the present invention can be any material known in the art capable of forming an ophthalmic device as described above. In one embodiment, an ophthalmic device includes ophthalmic devices formed from material not hydrophilic per se. Such devices are formed from materials known in the art and include, by way of example, polysiloxanes, perfluoropolyethers, fluorinated poly(meth)acrylates or equivalent fluorinated polymers derived, e.g., from other polymerizable carboxylic acids, polyalkyl (meth)acrylates or equivalent alkylester polymers derived from other polymerizable carboxylic acids, or fluorinated polyolefins, such as fluorinated ethylene propylene polymers, or tetrafluoroethylene, preferably in combination with a dioxol, e.g., perfluoro-2,2-dimethyl-1, 3-dioxol. Representative examples of suitable bulk materials include, but are not limited to, Lotrafilcon A, Neofocon, Pasifocon, Telefocon, Fluorsilfocon, Paflufocon, Silafocon, Elastofilcon, Fluorofocon or Teflon AF materials, such as Teflon AF 1600 or Teflon AF 2400 which are copolymers of about 63 to about 73 mol % of perfluoro-2,2-dimethyl-1,3-dioxol and about 37 to about 27 mol % of tetrafluoroethylene, or of about 80 to about 90 mol % of perfluoro-2,2-dimethyl-1,3-dioxol and about 20 to about 10 mol % of tetrafluoroethylene.

In another embodiment, an ophthalmic device includes ophthalmic devices formed from material hydrophilic per se, since reactive groups, e.g., carboxy, carbamoyl, sulfate, sulfonate, phosphate, amine, ammonium or hydroxy groups, are inherently present in the material and therefore also at the surface of an ophthalmic device manufactured therefrom. Such ophthalmic devices are formed from materials known in the art and include, by way of example, polyhydroxyethyl acrylate, polyhydroxyethyl methacrylate, polyvinyl pyrrolidone (PVP), polyacrylic acid, polymethacrylic acid, polyacrylamide, polydimethylacrylamide (pDMA), polyvinyl alcohol and the like and copolymers thereof, e.g., from two or more monomers selected from hydroxyethyl acrylate, hydroxyethyl methacrylate, N-vinyl pyrrolidone, acrylic acid, methacrylic acid, acrylamide, dimethyl acrylamide, vinyl alcohol and the like. Representative examples of suitable bulk materials include, but are not limited to, Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon, Nelfilcon, Atlafilcon, Balafilcon A, Hilafilcon A, Alphafilcon A, Bilafilcon B and the like.

In another embodiment, ophthalmic devices according to the present invention include ophthalmic devices which are formed from materials which are amphiphilic segmented copolymers containing at least one hydrophobic segment and at least one hydrophilic segment which are linked through a bond or a bridge member.

It is particularly useful to employ biocompatible materials herein including both soft and rigid materials commonly used for ophthalmic devices, including contact lenses. In general, non-hydrogel materials are hydrophobic polymeric materials that do not contain water in their equilibrium state. Typical non-hydrogel materials comprise silicone acrylics, such as those formed from a bulky silicone monomer (e.g., tris(trimethylsiloxy)silylpropyl methacrylate, commonly known as "TRIS" monomer), methacrylate end-capped poly (dimethylsiloxane) prepolymer, or silicones having fluoroalkyl side groups (polysiloxanes are also commonly known as silicone polymers).

On the other hand, hydrogel materials comprise hydrated, cross-linked polymeric systems containing water in an equilibrium state. Hydrogel materials contain about 5 weight percent water or more (up to, for example, about 80 weight percent). In one embodiment, hydrogel materials for ophthalmic devices, such as contact lenses, can contain at least one hydrophilic monomer such as one or more unsaturated carboxylic acids, vinyl lactams, amides, polymerizable amines, vinyl carbonates, vinyl carbamates, oxazolone monomers, copolymers thereof and the like and mixtures thereof. Useful amides include acrylamides such as N,N-dimethylacrylamide and N,N-dimethylmethacrylamide. Useful vinyl lactams include cyclic lactams such as N-vinyl-2-pyrrolidone. Examples of other hydrophilic monomers include hydrophilic prepolymers such as poly(alkene glycols) functionalized with polymerizable groups. Examples of useful functionalized poly(alkene glycols) include poly(diethylene glycols) of varying chain length containing monomethacrylate or dimethacrylate end caps. In a preferred embodiment, the poly(alkene glycol) polymer contains at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. In another embodiment, a hydrogel material can contain a siloxane-containing monomer and at least one of the aforementioned hydrophilic monomers and/or prepolymers.

Examples of other hydrogel materials include hydrophobic monomers. Suitable hydrophobic monomers (b) include ethylenically unsaturated hydrophobic monomers such as, for example, (meth)acrylates-containing hydrophobic monomers, N-alkyl (meth)acrylamides-containing hydrophobic monomers, alkyl vinylcarbonates-containing hydrophobic monomers, alkyl vinylcarbamates-containing hydrophobic monomers, fluoroalkyl (meth)acrylates-containing hydrophobic monomers, N-fluoroalkyl (meth)acrylamides-containing hydrophobic monomers, N-fluoroalkyl vinylcarbonates-containing hydrophobic monomers, N-fluoroalkyl vinylcarbamates-containing hydrophobic monomers, silicone-containing (meth)acrylates-containing hydrophobic monomers, (meth)acrylamides-containing hydrophobic monomers, vinyl carbonates-containing hydrophobic monomers, vinyl carbamates-containing hydrophobic monomers, styrenic-containing hydrophobic monomers, polyoxypropylene (meth)acrylate-containing hydrophobic monomers and the like and mixtures thereof. As used herein, the term "(meth)" denotes an optional methyl substituent. Thus, terms such as "(meth)acrylate" denotes either methacrylate or acrylate, and "(meth)acrylamide" denotes either methacrylamide or acrylamide.

In one embodiment, the ophthalmic device is a silicone hydrogel contact lens material. Silicone hydrogels generally have a water content greater than about 5 weight percent and more commonly between about 10 to about 80 weight percent. Such materials are usually prepared by polymerizing a mixture containing at least one silicone-containing monomer and at least one hydrophilic monomer as described above. Typically, either the silicone-containing monomer or the hydrophilic monomer functions as a crosslinking agent (a crosslinker being defined as a monomer having multiple polymerizable functionalities) or a separate crosslinker may be employed. Applicable silicone-containing monomers for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

Representative examples of applicable silicon-containing monomers include bulky polysiloxanylalkyl(meth)acrylic monomers. An example of a bulky polysiloxanylalkyl(meth) acrylic monomer is represented by the structure of Formula I:

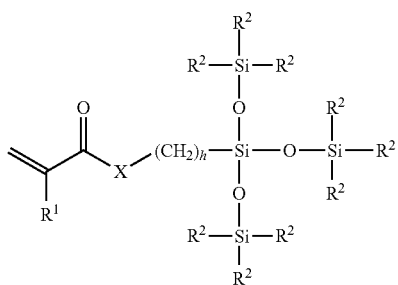

(I)

wherein X denotes —O— or —NR— wherein R denotes hydrogen or a $C_1$-$C_4$ alkyl; each $R^1$ independently denotes hydrogen or methyl; each $R^2$ independently denotes a lower alkyl radical, phenyl radical or a group represented by

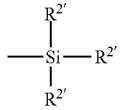

wherein each $R^{2'}$ independently denotes a lower alkyl or phenyl radical; and h is 1 to 10.

Representative examples of other applicable silicon-containing monomers include, but are not limited to, bulky polysiloxanylalkyl carbamate monomers as generally depicted in Formula Ia:

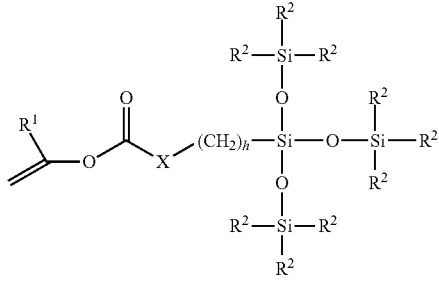

(Ia)

wherein X denotes —NR—; wherein R denotes hydrogen or a $C_1$-$C_4$ alkyl; $R^1$ denotes hydrogen or methyl; each $R^2$ independently denotes a lower alkyl radical, phenyl radical or a group represented by

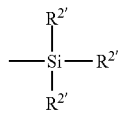

wherein each $R^{2'}$ independently denotes a lower alkyl or phenyl radical; and h is 1 to 10, and the like.

Examples of bulky monomers are 3-methacryloyloxypropyltris(trimethyl-siloxy)silane or tris(trimethylsiloxy)silylpropyl methacrylate, sometimes referred to as TRIS and tris(trimethylsiloxy)silylpropyl vinyl carbamate, sometimes referred to as TRIS-VC and the like and mixtures thereof.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris(trimethyl siloxy)silyl]propyl allyl carbamate; 3-[tris (trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like and mixtures thereof.

Another class of silicon-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacryates in Polyurethane-Polysiloxane Hydrogels," Journal of Applied Polymer Science, Vol. 60, 1193-1199 (1996). PCT Published Application No. WO 96/31792 discloses examples of such monomers, which disclosure is hereby incorporated by reference in its entirety. Further examples of silicone urethane monomers are represented by Formulae II and III:

$$E(*D*A*D*G)_a*D*A*D*E'; \text{ or} \qquad (II)$$

$$E(*D*G*D*A)_a*D*A*D*E'; \text{ or} \qquad (III)$$

wherein:

D independently denotes an alkyl diradical, an alkyl cycloalkyl diradical, a cycloalkyl diradical, an aromatic diradical or an alkylaromatic diradical having 6 to about 30 carbon atoms;

G independently denotes an alkyl diradical, a cycloalkyl diradical, an alkyl cycloalkyl diradical, an aromatic diradical or an alkylaromatic diradical having 1 to about 40 carbon atoms and which may contain ether, thio or amine linkages in the main chain;

* denotes a urethane or ureido linkage;

a is at least 1;

A independently denotes a divalent polymeric radical of Formula IV:

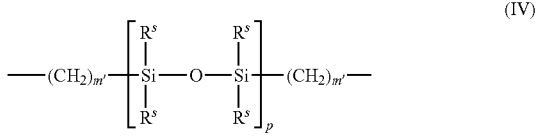

(IV)

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula V:

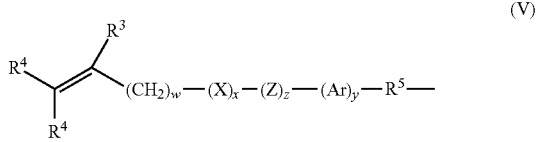

(V)

wherein: $R^3$ is hydrogen or methyl;
$R^4$ is hydrogen, an alkyl radical having 1 to 6 carbon atoms, or a —CO—Y—$R^6$ radical wherein Y is —O—, —S— or —NH—;
$R^5$ is a divalent alkylene radical having 1 to about 10 carbon atoms;
$R^6$ is a alkyl radical having 1 to about 12 carbon atoms;
X denotes —CO— or —OCO—;
Z denotes —O— or —NH—;
Ar denotes an aromatic radical having about 6 to about 30 carbon atoms;
w is 0 to 6; x is 0 or 1; y is 0 or 1; and z is 0 or 1.

A preferred silicone-containing urethane monomer is represented by Formula VI:

In another embodiment of the present invention, a silicone hydrogel material comprises (in bulk, that is, in the monomer mixture that is copolymerized) about 5 to about 50 percent, and preferably about 10 to about 25, by weight of one or more silicone macromonomers, about 5 to about 75 percent, and preferably about 30 to about 60 percent, by weight of one or more polysiloxanylalkyl (meth)acrylic monomers, and about 10 to about 50 percent, and preferably about 20 to about 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 discloses additional unsaturated groups, including acryloxy or methacryloxy. Fumarate-containing materials such as those disclosed in U.S. Pat. Nos. 5,310,779; 5,449,729 and 5,512,205 are also useful substrates in accordance with the invention. The silane macromonomer may be a silicon-containing vinyl carbonate or vinyl carbamate or a polyurethane-polysiloxane having one or more hard-soft-hard blocks and end-capped with a hydrophilic monomer.

Another class of representative silicone-containing monomers includes fluorinated monomers. Such monomers have been used in the formation of fluorosilicone hydrogels to reduce the accumulation of deposits on contact lenses made therefrom, as disclosed in, for example, U.S. Pat. Nos. 4,954,587; 5,010,141 and 5,079,319. Also, the use of silicone-containing monomers having certain fluorinated side groups, i.e., —($CF_2$)—H, have been found to improve compatibility between the hydrophilic and silicone-containing monomeric units. See, e.g., U.S. Pat. Nos. 5,321,108 and 5,387,662.

The above silicone materials are merely exemplary, and other materials for use as substrates that can benefit by having a UV blocker according to the present invention and have been disclosed in various publications and are being continuously developed for use in contact lenses and other

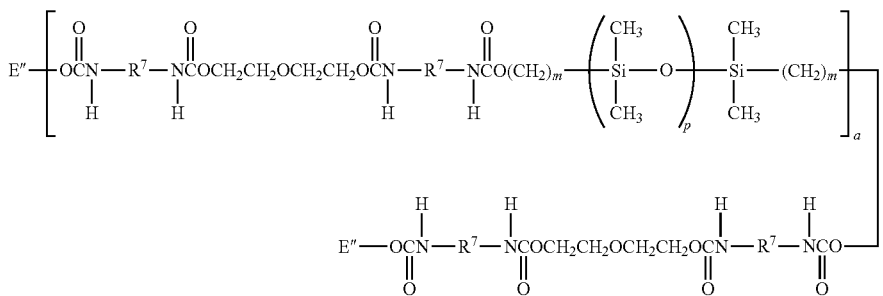

wherein m is at least 1 and is preferably 3 or 4, a is at least 1 and preferably is 1, p is a number which provides a moiety weight of about 400 to about 10,000 and is preferably at least about 30, $R^7$ is a diradical of a diisocyanate after removal of the isocyanate group, such as the diradical of isophorone diisocyanate, and each E" is a group represented by:

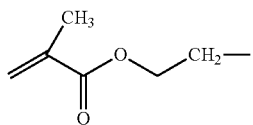

medical devices can also be used. For example, an ophthalmic device can be formed from at least a cationic monomer such as cationic silicone-containing monomer or cationic fluorinated silicone-containing monomers.

Ophthalmic devices such as contact lenses for application of the present invention can be manufactured employing various conventional techniques, to yield a shaped article having the desired posterior and anterior lens surfaces. Various processes are known for curing a monomeric mixture in the production of contact lenses including, by way of example, spincasting and static casting. For example, spincasting methods involve charging the monomer mixture in an open faced mold having a concave bottom surface, i.e., a one-piece mold, and spinning the mold in a controlled manner while exposing the monomer mixture to light, such as UV light. Static casting methods involve charging the monomer mixture between two mold sections, one mold section shaped to form the anterior lens surface and the other mold section shaped to form the posterior lens surface, and curing the monomer mixture while retained in the mold assembly to form a lens, for example, by free radical polymerization of the mixture. Spincasting methods are disclosed in U.S. Pat. Nos. 3,408,429 and 3,660,545, and static casting methods are disclosed in U.S. Pat. Nos. 4,113,224, 4,197,266, and 5,271,875. Additionally, the monomer mixtures may be cast in the shape of rods or buttons, which are then lathe cut into a desired lens shape.

Polymerization may be facilitated by exposing the mixture to heat and/or radiation, such as ultraviolet light, visible light, or high energy radiation. A polymerization initiator may be included in the mixture to facilitate the polymerization step. Representative examples of free radical thermal polymerization initiators include organic peroxides such as acetyl peroxide, lauroyl peroxide, decanoyl peroxide, stearoyl peroxide, benzoyl peroxide, tertiaromaticbutyl peroxypivalate, peroxydicarbonate, and the like and azo compounds such as 2,2'-azobisisobutyronitrile (AIBN), 1,1'-azobis(cyclohexanecarbonitrile), 4,4'-azobis(4-cyanovaleric acid), and the like. Representative UV initiators are those known in the art and include benzoin methyl ether, benzoin ethyl ether, Darocure 1173, 1164, 2273, 1116, 2959, 3331 (EM Industries) and Irgacure 651 and 184 (BASF), and the like. Representative examples of visible light initiators include phosphine oxides such as Irgacure 819, Darocure TPO (BASF), Lucirin TPO, Lucirin TPO-L (BASF), etc. Generally, the initiator will be employed in the mixture at a concentration of about 0.01 to about 5 percent by weight of the total monomer mixture.

Generally, polymerization under UV or visible light ('blue light') curing polymerization conditions can be carried out for about 15 minutes to about 60 minutes and under an inert atmosphere of, for example, nitrogen or argon. Polymerization under thermal curing conditions generally requires higher temperatures, e.g., about 40 to about 120° C.) for a time period of about 10 to about 72 hours.

Following casting, the polymerization product (ophthalmic device) is dry released from the mold. In the case where the mold is a two-part mold assembly, including a posterior mold half and an anterior mold half, dry release is carried out when one of the mold halves is removed, i.e., de-capped, with the cast polymerization product remaining adhered to the other mold half. In many processes, it is desired that the polymerization product remains with the anterior mold half. In general, a dry release process involves releasing the polymerization product from the mold half in a dry state and without adding aqueous media. While not wishing to be bound by theory, it is believed that the boric acid ester of a $C_1$ to $C_8$ monohydric alcohol cross-links with the polymerization product during curing such that the polymerization product possesses a sufficient hardness to allow it to be dry released from the mold. One skilled in the art would readily appreciate that the term "sufficient hardness" means that the resulting polymerization product is not too soft so that it tears during the dry release process (e.g., when being removed from mold with mechanical grippers) or is too brittle such that it shatters or breaks upon being subjected to the mechanical forces encountered during the dry release process.

In one embodiment, the polymerization product can be dry released by simply removing the polymerization product from the mold in a dry state. In another embodiment, dry release is accomplished by way of mechanical actions in which the polymerization product is removed mechanically from the molds using mechanical grippers such as tweezers, taking a precaution of not to tear the polymerization product. In the event that mechanical removal cannot be carried out, the mold half containing the polymerization product is mechanically deformed to forcibly dry release it.

Once the ophthalmic devices such as contact lenses are dry released, they can then be subjected to optional machining operations. Other optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

The resulting ophthalmic device thus formed is then subjected to the steps of the method according to the present invention to incorporate the UV blocker into the device. In step (a) of the method according to the present invention, the ophthalmic device is soaked in one or more first solvent solutions for a time period sufficient to swell the ophthalmic device. In general, the one or more first solvent solutions include a solvent capable of swelling the ophthalmic lens. In one embodiment, the one or more first solvent solutions include, for example, a low molecular weight alcohol solvent, an aliphatic hydrocarbon solvent, a cycloaliphatic hydrocarbon solvent, a ketone solvent, a nitrile solvent, an ether solvent, an amido group-containing solvent and mixtures thereof. Suitable low molecular weight alcohols include, for example, low molecular weight alcohols having about 1 to about 13 carbon atoms and/or a molecular weight of no greater than about 200. A suitable low molecular alcohol can be selected from a variety of low-molecular-weight monohydric alcohols, each comprising about 1 to about 13 carbon atoms. Suitable monohydric alcohols include, for example, methanol, ethanol, propanol, isopropyl alcohol, butanol, isobutyl alcohol, tert-butyl alcohol, hexanol, 2-ethylhexanol, dodecanol, and the like. Suitable aliphatic or cycloaliphatic hydrocarbon solvents include, for example, pentane, hexane, heptane, cyclohexane and the like.

Suitable ketone solvents include, for example, acetone, methyl ethyl ketone, diethyl ketone, methyl propyl ketone, methyl isopropyl ketone, ethyl propyl ketone, ethyl isopropyl ketone, dipropyl ketone, diisopropyl ketone, methyl butyl ketone, methyl isobutyl ketone, methyl sec butyl ketone, methyl tert-butyl ketone, ethyl butyl ketone, ethyl isobutyl ketone, ethyl sec-butyl ketone, ethyl tert-butyl ketone, propyl butyl ketone, isopropyl butyl ketone, propyl isobutyl ketone, propyl sec-butyl ketone, propyl tert butyl ketone, isopropyl isobutyl ketone, isopropyl sec-butyl ketone, isopropyl tert-butyl ketone, dibutyl ketone, diisobutyl ketone, di-sec-butyl ketone, di-tert-butyl ketone, butyl isobutyl ketone, butyl sec-butyl ketone, butyl tert-butyl ketone, isobutyl sec-butyl ketone, isobutyl tert-butyl ketone, sec-butyl tert-butyl ketone, 5-heptanone, 5-methyl-2-hexanone (methyl isoamyl ketone), 4-methyl-2-hexanone, 3-methyl-2-hexanone, 3,4-dimethyl-2-pentanone, 3,3-dimethyl-2-pentanone, 4,4-dimethyl-2-pentanone, 3-octanone, 4-methyl-3-heptanone, 5-methyl-3-heptanone, 6-methyl-3-heptanone, 4,4-dimethyl-3-hexanone, 4,5-dimethyl-3-hexanone, 5,5-dimethyl-3-hexanone, 4-nonanone, 5-methyl-4-octanone, 6-methyl-4-octanone, 7-methyl-4-octanone, 5,5-dimethyl-4-neptanone, 5,6-dimethyl-4-heptanone, 6,6-dimethyl-4-heptanone, 2-undecanone, cyclopropanone, cyclobutanone, cyclopentanone, cyclohexanone, cycloheptanone, cyclooctanone, cyclononanone, cyclodecanone, cycloundecanone, cyclododecanone and the like and combinations thereof. In one embodiment, a ketone solvent is acetone.

Suitable nitrile solvents include, for example, saturated or unsaturated aliphatic, alicyclic, or aromatic compounds containing a nitrile group. Included within the nitriles are compounds containing heteroatom such as those selected from Groups 13, 14, 15, 16 and 17 of the Periodic Table of Elements. Representative examples of nitriles for use herein include acetonitrile; propionitrile; isopropionitrile; butyronitrile; isobutyronitrile; valeronitrile; isovaleronitrile; trimethylacetonitrile; hexanenitrile; heptanenitrile; heptyl cyanide; octyl cyanide; undecanenitrile; malononitrile; succinonitrile; glutaronitrile; adiponitrile; sebaconitrile; allyl cyanide; acrylonitrile; crotononitrile; methacrylonitrile; fumaronitrile; tetracyanoethylene; cyclopentanecarbonitrile; cyclohexanecarbonitrile; dichloroacetonitrile; fluoroacetonitrile; trichloroacetonitrile; benzonitrile; benzyl cyanide; 2-methylbenzyl cyanide; 2-chlorobenzonitrile; 3-chlorobenzonitrile; 4-chlorobenzonitrile; o-tolunitrile; m-tolunitrile; p-tolunitrile and the like and mixtures thereof. In one embodiment, a a nitrile solvent is acetonitrile.

Suitable ether solvents include, for example, dialkyl ethers wherein the alkyl groups are the same or different and are from 1 to about 12 carbon atoms. Representative examples of an ether solvent include dimethylether, diethylether, di-i-propylether; dioxane, tetrahydrofuran, pyran and the like and mixtures thereof. In one embodiment, an ether solvent is tetrahydrofuran.

Suitable amido group-containing solvents include, for example, dimethyl formamide, N-methyl formanilide, N-formyl piperidine, N-formyl morpholine, dimethyl acetamide, N-methyl pyrrolidone, N,N-dimethyl benzamide and mixtures thereof. In one embodiment, an amido group-containing solvent is N-methyl pyrrolidone.

In one embodiment, the one or more first solvent solutions can further include water in combination with any of the foregoing first solvents. For example, the one or more first solvent solutions can be a blend containing from about 25 wt. % to about 75 wt. % one or more first solvent solutions and from about 75 wt. % to about 25 wt. % water. In another embodiment, a blend can contain from about 40 wt. % to about 60 wt. % one or more first solvent solutions and from about 60 wt. % to about 40 wt. % water.

The ophthalmic device is soaked in the one or more first solvent solutions for a time period sufficient to swell the ophthalmic device. In general, the ophthalmic device is soaked in the one or more first solvent solutions for a time period ranging from about 5 minutes to about 120 minutes. In one embodiment, the ophthalmic device is soaked in the one or more first solvent solutions for a time period ranging from about 5 minutes to about 60 minutes. In one embodiment, the ophthalmic device is soaked in the one or more first solvent solutions for a time period ranging from about 10 minutes to about 35 minutes.

In one embodiment, the ophthalmic device is soaked in a series of the one or more first solvent solutions. For example, the ophthalmic device is first soaked in the one or more first solvent solutions or blend of the one or more first solvents and water as discussed hereinabove for a time period ranging from about 5 minutes to about 30 minutes, or from about 5 minutes to about 20 minutes. Next, the ophthalmic device is removed from the solution or blend and soaked in another solvent solution of any of the foregoing one or more first solvents for a time period ranging from about 5 minutes to about 120 minutes. In one embodiment, the ophthalmic device is soaked in the another solvent solution for a time period ranging from about 5 minutes to about 60 minutes. In one embodiment, the ophthalmic device is soaked in the another solvent solution for a time period ranging from about 10 minutes to about 35 minutes.

In step (b) of the method according to the present invention, the swelled ophthalmic device is soaked in one or more second solvent solutions comprising a UV blocker to de-swell the ophthalmic device and entrap the UV blocker in the ophthalmic device. In general, the one or more second solvent solutions include any solvent capable of dissolving the UV blocker. Suitable second solvent solutions include, for example, water and any of the foregoing low molecular weight alcohol solvent, aliphatic hydrocarbon solvent, cycloaliphatic hydrocarbon solvent, ketone solvent, nitrile solvent, ether solvent, and amido group-containing solvents discussed hereinabove.

In one embodiment, the one or more second solvent solutions include a blend of water together with any of the low molecular weight alcohol solvents, aliphatic hydrocarbon solvents, cycloaliphatic hydrocarbon solvents, ketone solvents, nitrile solvents, ether solvents, and amido group-containing solvent. For example, the one or more second solvent solutions can be a blend containing from about 25 wt. % to about 75 wt. % one or more second solvent solutions such as a low molecular weight alcohol and from about 75 wt. % to about 25 wt. % water. In another embodiment, a blend can contain from about 40 wt. % to about 60 wt. % one or more second solvent solutions such as a low molecular weight alcohol and from about 60 wt. % to about 40 wt. % water. When using a blend, the UV blocker is first added to the one or more second solvent solutions to form a solution. Next, water is added to the solution in an amount such that the UV blocker does not precipitate out of the solution.

In one embodiment, a UV blocker to be incorporated into the ophthalmic device is a benzotriazole. For example, a benzotriazole for use herein can a benzotriazole of the general formula VII:

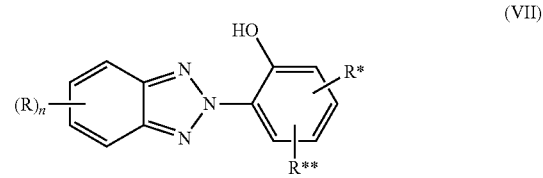

(VII)

wherein each R is independently hydrogen, a halogen, an —O— group, a nitro group, a nitrile group, an alkoxy group, a hydroxyl group, an alkyl group, a cycloalkyl group, an alkynyl group, an alkene group, an aromatic group, an amine group, a carbonyl group, and a heterocyclic group, R* is a linear or branched $C_3$ to $C_{28}$ alkyl, a nitro group, a nitrile group, an alkoxy group, a hydroxyl group, a cycloalkyl group, an alkenyl group, an alkenyl group, an alkynyl group, an aromatic group, an amine group, a carbonyl group, and a heterocyclic group, and R** is a linear $C_1$ to $C_8$ alkyl group, a branched $C_3$ to $C_8$ alkyl, a halogen, a nitro group, a nitrile group, an alkoxy group, a hydroxyl group, a cycloalkyl group, an alkenyl group, an alkynyl group, an aromatic group, an amine group, a carbonyl group, and a heterocyclic group.

Representative examples of halogen groups include, by way of example, Cl, I, F, and Br. Representative examples of alkoxy groups for use herein include, by way of example, an alkyl group as defined herein attached via oxygen linkage to the rest of the molecule, i.e., of the general formula —OR$^4$, wherein R$^4$ is an alkyl, cycloalkyl, or aromatic group as defined herein, e.g., —OCH$_3$, —OC$_2$H$_5$, or —OC$_6$H$_5$ which may be substituted or unsubstituted, and the like.

Representative examples of alkyl groups for use herein include, by way of example, a straight or branched hydrocarbon chain radical containing carbon and hydrogen atoms of from 1 to about 30 carbon atoms with or without unsaturation, to the rest of the molecule, e.g., methyl, ethyl, n-propyl, 1-methylethyl (isopropyl), n-butyl, n-pentyl, etc., and the like.

Representative examples of cycloalkyl groups for use herein include, by way of example, a substituted or unsubstituted non-aromatic mono or multicyclic ring system of about 3 to about 30 carbon atoms such as, for example, cyclopropyl, cyclobutyl, cyclopentyl, cyclohexyl, perhydronapththyl, adamantyl and norbornyl groups bridged cyclic group or sprirobicyclic groups, e.g., sprio-(4, 4)-non-2-yl and the like, optionally containing one or more heteroatoms, e.g., O and N, and the like.

Representative examples of alkenyl groups for use herein include, by way of example, a straight or branched hydrocarbon chain radical containing from about 3 to about 30 carbon atoms with at least one carbon-carbon double bond such as, for example, propenyl, butenyl, pentenyl and the like.

Representative examples of alkynyl groups for use herein include, by way of example, a straight or branched hydrocarbon chain radical containing from about 3 to about 30 carbon atoms with at least one carbon-carbon triple bond such as, for example, propynyl, butynyl, pentynyl and the like.

Representative examples of heterocyclic groups for use herein include, by way of example, a substituted or unsubstituted stable 3 to about 15 membered ring radical, containing carbon atoms and from one to five heteroatoms, e.g., nitrogen, phosphorus, oxygen, sulfur and mixtures thereof. Suitable heterocyclic ring radicals for use herein may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. Examples of such heterocyclic groups include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, isochromanyl and the like and mixtures thereof.

Representative examples of aromatic groups for use herein include, by way of example, a substituted or unsubstituted monoaromatic or polyaromatic radical containing from about 5 to about 30 carbon atoms such as, for example, phenyl, naphthyl, tetrahydronapthyl, indenyl, biphenyl and the like, optionally containing one or more heteroatoms, e.g., O and N, and the like.

Representative examples of amine-containing groups for use herein include, by way of example, an amine of the general formula —R$^5$NR$^6$R$^7$ wherein R$^5$, R$^6$ and R$^7$ are independently hydrogen or a C$_1$-C$_{30}$ hydrocarbon such as, for example, alkyl groups, aromatic groups, or cycloalkyl groups as defined herein, and the like.

In one embodiment, R is hydrogen, R* is a branched C$_3$ to C$_8$ alkyl group and R** is a branched C$_3$ to C$_8$ alkyl group. In one embodiment, R is hydrogen, R* is a linear C$_8$ to C$_{28}$ alkyl group and R** is a linear C$_1$ to C$_8$ alkyl group. In one embodiment, R is hydrogen, R* is a linear C$_{10}$ to C$_{28}$ alkyl group and R** is a linear C$_1$ to C$_8$ alkyl group. In one embodiment, R is hydrogen, R* is a linear C$_{10}$ to C$_{22}$ alkyl group and R** is a linear C$_1$ to C$_3$ alkyl group. In one embodiment, R* is a branched C$_3$ to C$_8$ alkyl group and R** is a branched C$_3$ to C$_8$ alkyl group. In one embodiment, R* is a linear C$_8$ to C$_{28}$ alkyl group and R** is a linear C$_1$ to C$_8$ alkyl group. In one embodiment, R* is a linear C$_{10}$ to C$_{28}$ alkyl group and R** is a linear C$_1$ to C$_8$ alkyl group. In one embodiment, R* is a linear C$_{10}$ to C$_{22}$ alkyl group and R** is a linear C$_1$ to C$_3$ alkyl group. In one embodiment, each of R* and R** are positioned on the aromatic ring to provide a sterically hindered benzotriazole. In one embodiment, each of R* and R** are positioned on the aromatic ring in the meta position. One preferred benzotriazole is of the general formula VIII:

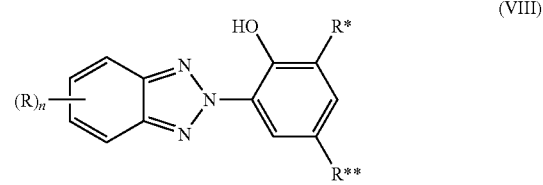

(VIII)

wherein R, R* and R** have the aforestated meanings.

Representative examples of UV blockers for use herein include, but are not limited to, 2-(2H-benzotriazole-2-yl)-6-dodecyl-4-methylphenol and 2-(2H-benzotriazole-2-yl)-4,6-ditert-pentylphenol. The UV blockers for use herein are known, for example, U.S. Pat. No. 9,075,187, and either commercially available from such sources as, for example, BASF, and Sigma Aldrich, or can be made by methods within the purview of one skilled in the art.

In general, the UV blocker is present in the one or more second solvent solutions in an amount ranging from about 0.05 to about 3 wt. % or from about 0.05 to about 0.75 wt. %.

The ophthalmic device is soaked in the one or more second solvent solutions for a time period sufficient to de-swell the ophthalmic device and entrap the UV blocker. In general, the ophthalmic device is soaked in the one or more second solvent solutions for a time period ranging from about 5 minutes to about 120 minutes. In one embodiment, the ophthalmic device is soaked in the one or more second solvent solutions for a time period ranging from about 10 minutes to about 35 minutes.

In one embodiment, the ophthalmic device is soaked in a series of the one or more second solvent solutions. For example, the ophthalmic device is first soaked in the one or more second solvent solutions comprising the low molecular weight alcohol solvent and UV blocker for a time period ranging from about 5 minutes to about 20 minutes. Next, the ophthalmic device is removed from the solvent solution and further soaked in another solvent solution comprising a blend of the same or different second low molecular weight alcohol solvent and water and UV blocker for a time period ranging from about 5 minutes to about 20 minutes.

After the ophthalmic device has been de-swelled, the ophthalmic device is removed and optionally soaked in one more series of water solutions to further de-swell the device. In general, the ophthalmic device is soaked in the one or more water solutions for a time period ranging from about 5 minutes to about 20 minutes.

In step (c), the de-swelled ophthalmic device is sterilized. In one embodiment, the de-swelled ophthalmic device is sterilized by submerging the de-swelled ophthalmic device in a borate buffered saline and then subjecting it to autoclave conditions for at least about 5 minutes, or at least about 20 minutes or at least 24 hours or up to about 72 hours. The sterilized ophthalmic device is then rinsed with water and positioned in their packaging with borate buffered saline. The package is sealed and again the ophthalmic device is subjected to autoclave conditions.

Alternatively, the de-swelled ophthalmic device can be placed in a container that includes a receptacle portion to hold the de-swelled ophthalmic device and a sterile packaging solution. Examples of the container are conventional ophthalmic device blister packages. This receptacle, containing the de-swelled ophthalmic device immersed in the solution, is hermetically sealed, for example, by sealing lidstock on the package over the receptacle. For example, the lidstock is sealed around a perimeter of the receptacle. The solution and the de-swelled ophthalmic device are sterilized while sealed in the package receptacle. Examples of sterilization techniques include subjecting the solution and the de-swelled ophthalmic device to thermal energy, microwave radiation, gamma radiation or ultraviolet radiation. A specific example involves heating the solution and the de-swelled ophthalmic device, while sealed in the package container, to a temperature of at least 100° C., or at least 120° C., such as by autoclaving.

In one embodiment, a photochromic material is also incorporated into the ophthalmic device. In some embodiments, it is advantageous if the photochromic material is broad band. A broadband photochromic material is defined herein as a material that blocks at least 50% of light for a band of at least 200 nm of the visible wavelengths at high brightness. (The band of 200 nm may be continuous in the visible band or not.) For example, naphthopyrans such as (3H-naphtho [2,1-b]pyran, 2H-naphtho [1,2-b]pyrans may be used as broadband photochromic materials. In some embodiments, the broadband photochromic material may be a neutral density photochromic material that is presently known or later developed. Such neutral density materials block light nearly uniformly across at least the visible spectrum at least some light levels. It will be appreciated that the spectral response of a given chromophore may change as a function of time of exposure to light, and as a function of the intensity of the light.

In some embodiments, a photochromic material having a non-uniform spectral response (i.e., a non-neural density material) may provide advantages. A photochromic material may block more light in longer visible wavelengths relative to light blocked in the short visible wavelengths. For example, the photochromic material may be a low pass filter in the visible wavelengths.

Alternatively, the photochromic material may block more light in shorter visible wavelengths relative to light blocked in the longer visible wavelengths. For example, the photochromic material may be a high pass filter in the visible wavelengths. For example, in such embodiments, a blue blocker such as Azo-dyes, 3,3-dianysl-6-piperidino-3H-naphtho [2,1-b]pyran available from James Robinson Ltd. or Photosol 5-3 (yellow) available from PPG Industries may be used. In another embodiment, a blue blocker such as a hydroxy acridone may be used. The high pass photochromic material may be any other suitable photochromic material that is presently known or later developed.

In yet a further alternative, the photochromic material may block more light in longer visible wavelengths and in the shorter visible wavelengths relative to light blocked in the middle visible wavelengths. For example, the photochromic material may be a band pass filter in the visible wavelengths.

In yet a further alternative, the photochromic material may block more light in the middle visible wavelengths relative to light blocked in longer visible wavelengths and in the shorter visible wavelengths. For example, the photochromic material may be a notch filter in the visible wavelengths.

The photochromic material may be incorporated into the ophthalmic device by soaking the swelled ophthalmic device obtained from step (a) in one or more third solvent solutions containing the photochromic material. In general, the one or more third solvent solutions include a solvent capable of dissolving the photochromic material. Suitable one or more third solvent solutions include, for example, a ketone solvent as discussed above, and the like. In one embodiment, a ketone solvent is acetone. The one or more third solvent solutions will further contain one or more of the low molecular weight alcohol solvents as discussed hereinabove.

In general, the photochromic material is present in the one or more third solvent solutions in an amount ranging from about 0.05 to about 3 wt. % or from about 0.05 to about 0.75 wt. %. The ophthalmic device is soaked in the one or more third solvent solutions for a time period sufficient to entrap the photochromic material in the ophthalmic device. In general, the ophthalmic device is soaked in the one or more third solvent solutions for a time period ranging from about 5 minutes to about 120 minutes or from about 10 minutes to about 35 minutes.

The following examples are provided to enable one skilled in the art to practice the invention and are merely illustrative of the invention. The examples should not be read as limiting the scope of the invention as defined in the claims.

In the examples, the following abbreviations are used.

Hydroxy acridone—a compound derived from the structure:

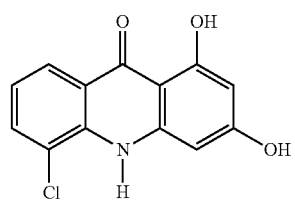 [SMILES: O=c1c2cccc(Cl)c2[nH]c2cc(O)cc(O)c12]

B12T—2-(2H-benzotriazol-2-yl)-6-dodecyl-4-methylphenol having the structure:

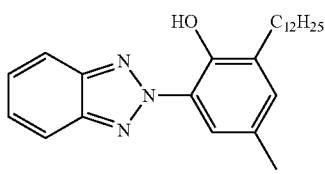

BTDT—2-(2H-Benzotriazol-2-yl)-4,6-di-tert-pentylphenol having the structure:

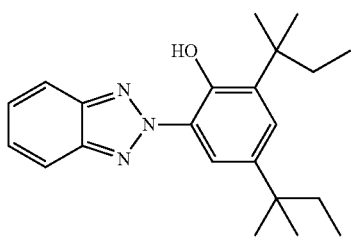 [SMILES: CCC(C)(C)c1cc(-n2nc3ccccc3n2)c(O)c(C(C)(C)CC)c1]

Methyl triazole—2-(2-hydroxy-5-methylphenyl)benzotriazole having the structure:

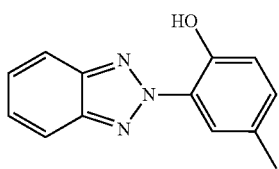 [SMILES: Cc1ccc(O)c(-n2nc3ccccc3n2)c1]

BTT—2-(2H-benzotriazol-2-yl)-4-(1,1,3,3-tetramethylbutyl) phenol having the structure:

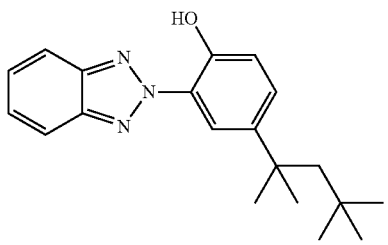 [SMILES: CC(C)(C)CC(C)(C)c1ccc(O)c(-n2nc3ccccc3n2)c1]

Example 1

First a 0.5 wt. % blue blocker solution in a 30:70 acetone:IPA was prepared by adding 0.0538 g of hydroxy acridone as the blue blocker into a 20 mL Vial, followed by 3.3147 g of acetone and 6.6828 g of IPA. This solution was then stirred until the blocker was fully dissolved.

Next, a nesofilcon-A lens was soaked for 10 minutes in the blue blocker solution, followed by soaking the lens for 15 minutes in a 100% deionized water and then sterilized in a steam sterilizer for 30 minutes at 121° C. with a 30 minute ramp to temperature. The lens was then tested for UV absorbance and found to block 50% of blue light in the 415 to 450 nm range in addition to 95% of UVA and 99.5% of UVB using ISO 18369-4:2017.

Example 2

Two UV solutions were prepared. First a 0.7% UV solution in IPA (solution-1) was prepared by adding 3.5 g of B12T as the UV blocker into a 1 L beaker, followed by 500 g of IPA. This solution was then stirred until the blocker was fully dissolved. Next, a solution of 0.1% UV blocker in 50:50 IPA:$H_2O$ (solution-2) was prepared by adding 0.5 g of 2 B12T into a 1 L beaker, followed by 250 g of IPA. This mixture was then stirred until the blocker was fully dissolved, then 250 g of $H_2O$ was then slowly added to the solution.

A silicone hydrogel lens (samfilcon A) was first soaked for 10 minutes in a 50:50 isopropyl alcohol (IPA):$H_2O$ solution, followed by soaking the lens for 30 minutes in a 100% IPA solution. Next, the lens was soaked in solution-1 for 10 minutes, followed by soaking the lens in solution-2 for 10 minutes. The lens was then subjected to two 10 minute soakings in $H_2O$ and then sterilized in a steam sterilizer for 30 minutes at 121° C. with a 30 minute ramp to temperature. The lens was determined to demonstrate sufficient blocking of UV light to meet FDA Class I specifications for UV blocking.

Example 3

Two UV solutions were prepared. First a 0.8 wt. % UV solution in IPA (solution-1) was prepared by adding 4.0 g of BTT as the UV blocker into a 1 L beaker, followed by 500 g of IPA. This solution was then stirred until the blocker was fully dissolved. Next, a solution of 0.1% UV blocker in 50:50 IPA:$H_2O$ (solution-2) was prepared by adding 0.5 g of BTDT into a 1 L beaker, followed by 250 g of IPA. This mixture was then stirred until the blocker was fully dissolved, then 250 g of $H_2O$ was then slowly added to the solution.

A samfilcon A lens first soaked for 10 minutes in a 50:50 isopropyl alcohol (IPA):$H_2O$ solution, followed by soaking the lens for 30 minutes in a 100% IPA solution. Next, the lens was soaked in a solution-1 for 10 minutes, followed by soaking the lens in solution-2 for 10 minutes. The lens was then subjected to two 10 minute soakings in $H_2O$ and then sterilized in a steam sterilizer for 30 minutes at 121° C. with a 30 minute ramp to temperature. The lens was determined to demonstrate sufficient blocking of UV light to meet FDA Class I specifications for UV blocking.

Comparative Example A

Two UV solutions were prepared. First a 0.3 wt. % UV solution in IPA (solution-1) was prepared by adding 1.5 g of methyl triazole as the UV blocker into a 1 L beaker, followed by 500 g of IPA. This solution was then stirred until the blocker was fully dissolved. Next, a solution of 0.1% UV blocker in 50:50 IPA:$H_2O$ (solution-2) was prepared by adding 0.5 g of methyl triazole into a 1 L beaker, followed by 250 g of IPA. This mixture was then stirred until the blocker was fully dissolved, then 250 g of $H_2O$ was then slowly added to the solution.

A samfilcon A lens was first soaked for 10 minutes in a 50:50 isopropyl alcohol (IPA):$H_2O$ solution, followed by soaking the lens for 30 minutes in a 100% IPA solution. Next, the lens was soaked in a solution-1 for 10 minutes, followed by soaking the lens in solution-2 for 30 minutes.

The lens was then subjected to two 10 minute soakings in H$_2$O and then sterilized in a steam sterilizer for 30 minutes at 121° C. with a 30 minute ramp to temperature. The lens was then placed in a vial containing a borate buffer solution and subjected to autoclaving for 1 hour at 121° C. After 4 hours, the methyl triazole UV blocker crystallized in the lens.

Comparative Example B

Two UV solutions were prepared. First a 0.7% UV solution in IPA (solution-1) was prepared by adding 3.5 g of BTT as the UV blocker into a 1 L beaker, followed by 500 g of IPA. This solution was then stirred until the blocker was fully dissolved. Next, a solution of 0.1% UV blocker in 50:50 IPA:H$_2$O (solution-2) was prepared by adding 0.5 g of BTT into a 1 L beaker, followed by 250 g of IPA. This mixture was then stirred until the blocker was fully dissolved, then 250 g of H$_2$O was then slowly added to the solution.

A samfilcon A lens was first soaked for 10 minutes in a 50:50 isopropyl alcohol (IPA):H$_2$O solution, followed by soaking the lens for 30 minutes in a 100% IPA solution. Next, the lens was soaked in a solution-1 for 10 minutes, followed by soaking the lens in solution-2 for 10 minutes. The lens was then subjected to two 10 minute soakings in H$_2$O. The lens was then placed in a vial containing a borate buffer solution and subjected to autoclaving for 1 hour at 121° C. After 120 hours, the BTT UV blocker crystallized in the lens.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A method for preparing an ophthalmic device containing an ultraviolet (UV) blocker comprising:
   (a) soaking an ophthalmic device in one or more first solvent solutions to swell the ophthalmic device;
   (b) soaking the swelled ophthalmic device in one or more second solvent solutions comprising a UV blocker to de-swell the ophthalmic device and entrap the UV blocker in the ophthalmic device, wherein the UV blocker is a benzotriazole of formula I:

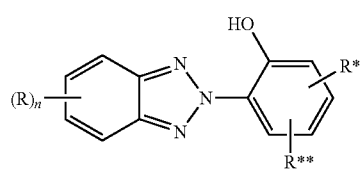

(I)

wherein each R is independently hydrogen, a halogen, an —O— group, a nitro group, a nitrile group, an alkoxy group, a hydroxyl group, an alkyl group, a cycloalkyl group, an alkynyl group, an alkene group, an aromatic group, an amine group, a carbonyl group, and a heterocyclic group, R* is a linear or branched C$_3$ to C$_{28}$ alkyl, a nitro group, a nitrile group, an alkoxy group, a hydroxyl group, a cycloalkyl group, an alkynyl group, an alkene group, an aromatic group, an amine group, a carbonyl group, and a heterocyclic group, and R** is hydrogen, a linear C$_1$ to C$_8$ alkyl group, a branched C$_3$ to C$_8$ alkyl, a halogen, a nitro group, a nitrile group, an alkoxy group, a hydroxyl group, a cycloalkyl group, an alkynyl group, an alkene group, an aromatic group, an amine group, a carbonyl group, and a heterocyclic group; and (c) sterilizing the de-swelled ophthalmic device.

2. The method of claim 1, wherein the one or more first solvent solutions comprise one or more of a low molecular weight alcohol solvent, an aliphatic hydrocarbon solvent, a cycloaliphatic hydrocarbon solvent, a ketone solvent, a nitrile solvent, an ether solvent, and an amido group-containing solvent.

3. The method of claim 2, wherein the low molecular weight alcohol solvent is a low molecular weight monohydric alcohol having about 1 to about 13 carbon atoms and/or a molecular weight of no greater than about 200.

4. The method of claim 1, wherein the one or more first solvent solutions comprise a blend of a low molecular weight alcohol solvent and water.

5. The method of claim 1, wherein the ophthalmic device is soaked in the one or more first solvent solutions for a time period ranging from about 5 minutes to about 120 minutes.

6. The method of claim 1, wherein step (a) comprises:
   (i) soaking the ophthalmic device in the one or more first solvent solutions comprising a blend of a low molecular weight alcohol solvent and water for a time period ranging from about 5 minutes to about 120 minutes; and
   (ii) soaking the ophthalmic device of step (i) in another solvent solution comprising one or more of the same or different low molecular weight alcohol solvent, an aliphatic hydrocarbon solvent, a cycloaliphatic hydrocarbon solvent, a ketone solvent, a nitrile solvent, an ether solvent, and an amido group-containing solvent for a time period ranging from about 5 minutes to about 60 minutes.

7. The method of claim 1, wherein for the benzotriazole of formula I, each R is hydrogen, R* is a branched C$_3$ to C$_8$ alkyl group and R** is a branched C$_3$ to C$_8$ alkyl group.

8. The method of claim 1, wherein for the benzotriazole of formula I, each R is hydrogen, R* is a linear C$_8$ to C$_{28}$ alkyl group and R** is a linear C$_1$ to C$_8$ alkyl group.

9. The method of claim 1, wherein for the benzotriazole of formula I, each R is hydrogen, R* is a linear C$_{10}$ to C$_{28}$ alkyl group and R** is a linear C$_1$ to C$_8$ alkyl group.

10. The method of claim 1, wherein the benzotriazole of formula I is a benzotriazole of formula II:

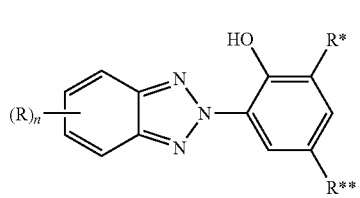

(II)

wherein R, R* and R** have the aforestated meanings.

11. The method of claim 1, wherein the benzotriazole of general formula I is selected from the group consisting of 2-(2H-benzotriazole-2-yl)-6-dodecyl-4-methylphenol and 2-(2H-benzotriazole-2-yl)-4,6-ditert-pentylphenol.

12. The method of claim 1, wherein the one or more second solvent solutions comprise one or more of water, a low molecular weight alcohol solvent, an aliphatic hydrocarbon solvent, a cycloaliphatic hydrocarbon solvent, a ketone solvent, a nitrile solvent, an ether solvent, and an amido group-containing solvent.

13. The method of claim 12, wherein the low molecular weight alcohol solvent is a low molecular weight monohydric alcohol having about 1 to about 13 carbon atoms and/or a molecular weight of no greater than about 200.

14. The method of claim 1, wherein the one or more second solvent solutions comprise a blend of a low molecular weight alcohol solvent and water.

15. The method of claim 1, wherein the UV blocker is present in the one or more second solvent solutions in an amount ranging from about 0.05 to about 3 wt. %, based on the total weight of the second solvent solution.

16. The method of claim 1, wherein the ophthalmic device is soaked in the one or more second solvent solutions for a time period ranging from about 5 minutes to about 120 minutes.

17. The method of claim 1, wherein step (b) comprises:
  (i) soaking the swelled ophthalmic device in the one or more second solvent solutions comprising a low molecular weight alcohol solvent and the UV blocker for a time period ranging from about 5 minutes to about 20 minutes; and
  (ii) soaking the ophthalmic device of step (i) in another solvent solution comprising a blend of the same or different low molecular weight alcohol solvent of the one or more second solvent solutions and water and the UV blocker for a time period ranging from about 5 minutes to about 20 minutes.

18. The method of claim 1, further comprising soaking the de-swelled ophthalmic device in one or more third solvent solutions comprising water prior to step (c).

19. The method of claim 1, wherein step (c) comprises autoclaving the ophthalmic device.

20. The method of claim 19, further comprising the step of applying a lid stock to a package containing the ophthalmic device prior to subjecting the ophthalmic device to a step of autoclaving.

21. The method of claim 1, further comprising incorporating a photochromic material into the ophthalmic device.

22. The method of claim 21, wherein the photochromic material is a blue blocker.

23. The method of claim 1, wherein the ophthalmic device is one or more of a contact lens, an intraocular lens and a corneal implant.

24. The method of claim 23, wherein the contact lens is a soft contact lens.

25. The method of claim 23, wherein the contact lens is a hydrogel contact lens.

26. The method of claim 23, wherein the contact lens is a silicone hydrogel contact lens.

27. The method of claim 23, wherein the contact lens is a rigid gas permeable contact lens.

28. An ophthalmic device comprising a UV blocker entrapped in a polymerization product of a monomeric mixture comprising one or more ophthalmic device-forming monomers, wherein the UV blocker is a benzotriazole of formula I:

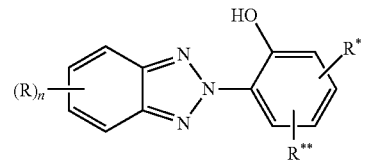

wherein each R is independently hydrogen, a halogen, an —O— group, a nitro group, a nitrile group, an alkoxy group, a hydroxyl group, an alkyl group, a cycloalkyl group, an alkynyl group, an alkene group, an aromatic group, an amine group, a carbonyl group, and a heterocyclic group, R* is a linear or branched $C_3$ to $C_{28}$ alkyl, a nitro group, a nitrile group, an alkoxy group, a hydroxyl group, a cycloalkyl group, an alkynyl group, an alkene group, an aromatic group, an amine group, a carbonyl group, and a heterocyclic group, and R** is a linear $C_1$ to $C_8$ alkyl group, a branched $C_3$ to $C_8$ alkyl, a halogen, a nitro group, a nitrile group, an alkoxy group, a hydroxyl group, a cycloalkyl group, an alkynyl group, an alkene group, an aromatic group, an amine group, a carbonyl group, and a heterocyclic group.

29. The ophthalmic device of claim 28, wherein for the benzotriazole of formula I, each R is hydrogen, R* is a branched $C_3$ to $C_8$ alkyl group and R** is a branched $C_3$ to $C_8$ alkyl group.

30. The ophthalmic device of claim 28, wherein for the benzotriazole of formula I, each R is hydrogen, R* is a linear $C_8$ to $C_{28}$ alkyl group and R** is a linear $C_1$ to $C_8$ alkyl group.

31. The ophthalmic device of claim 28, wherein for the benzotriazole of formula I, each R is hydrogen, R* is a linear $C_{10}$ to $C_{28}$ alkyl group and R** is a linear $C_1$ to $C_8$ alkyl group.

32. The ophthalmic device of claim 28, wherein the benzotriazole of formula I is a benzotriazole of formula II:

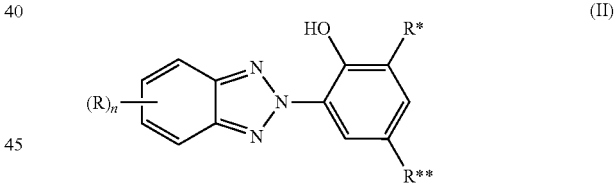

wherein R, R* and R** have the aforestated meanings.

33. The ophthalmic device of claim 28, further comprising a photochromic material entrapped in the ophthalmic device.

34. The ophthalmic device of claim 33, wherein the photochromic material is a blue blocker.

35. The ophthalmic device of claim 28, which is one or more of a contact lens, an intraocular lens and a corneal implant.

36. The ophthalmic device of claim 35, wherein the contact lens is one of a soft contact lens, a hydrogel contact lens and a rigid gas permeable contact lens.

37. The ophthalmic device of claim 28, demonstrating sufficient blocking of UV light to meet at least FDA Class II specifications for UV blocking.

38. The ophthalmic device of claim 28, demonstrating sufficient blocking of UV light to meet at least FDA Class I specifications for UV blocking.

* * * * *